US008636780B2

(12) United States Patent
Goble et al.

(10) Patent No.: US 8,636,780 B2
(45) Date of Patent: *Jan. 28, 2014

(54) LINE LOCK GRAFT RETENTION SYSTEM AND METHOD

(75) Inventors: E. Marlowe Goble, Logan, UT (US); T. Wade Fallin, Hyde Park, UT (US)

(73) Assignee: IMDS Corporation, Providence, UT (US)

( * ) Notice: Subject to any disclaimer, the term of this patent is extended or adjusted under 35 U.S.C. 154(b) by 1017 days.

This patent is subject to a terminal disclaimer.

(21) Appl. No.: 12/623,558

(22) Filed: Nov. 23, 2009

(65) Prior Publication Data

US 2010/0069926 A1 Mar. 18, 2010

Related U.S. Application Data

(63) Continuation of application No. 11/112,814, filed on Apr. 21, 2005, now Pat. No. 7,641,694, which is a continuation-in-part of application No. 11/030,462, filed on Jan. 6, 2005, now Pat. No. 7,488,347.

(51) Int. Cl.
*A61B 17/66* (2006.01)

(52) U.S. Cl.
USPC .......................................... 606/282

(58) Field of Classification Search
USPC ......... 606/300–305, 309, 310, 321, 232, 282; 623/13.11–13.18
See application file for complete search history.

(56) References Cited

U.S. PATENT DOCUMENTS

| | | |
|---|---|---|
| 3,409,014 A | 11/1968 | Shannon |
| 3,678,543 A | 7/1972 | Hobbs |
| 3,715,782 A | 2/1973 | Newell |
| 3,785,009 A | 1/1974 | Nysten |
| 3,880,166 A | 4/1975 | Fogarty |
| 3,910,281 A | 10/1975 | Kletschka et al. |
| 3,976,079 A | 8/1976 | Samuels et al. |
| 4,034,443 A | 7/1977 | Turner |
| 4,105,349 A | 8/1978 | Kupperman et al. |
| 4,280,435 A | 7/1981 | Loomis |
| 4,477,947 A | 10/1984 | Lyons |
| 4,479,271 A | 10/1984 | Bolesky et al. |

(Continued)

FOREIGN PATENT DOCUMENTS

| | | |
|---|---|---|
| EP | 861050 B1 | 6/2004 |
| EP | 1430840 A2 | 6/2004 |

(Continued)

*Primary Examiner* — Kevin T Truong
*Assistant Examiner* — Michael Araj
(74) *Attorney, Agent, or Firm* — G. Jo Hays; James Larson; James M. Pinkston

(57) ABSTRACT

A system for restoring articular cartilage has a cover, an anchor, and a tether that cooperate to retain graft tissue with respect to a graft site. The cover is attached to the anchor via the tether. The tether passes through a tunnel through a bone to which the articular cartilage is attached. The tunnel may be blind or may extend through the bone. The anchor is retained within the tunnel such that tension in the tether keeps the cover in place over the tissue graft. The anchor may receive the tether such that the tether can only pass through the anchor along one direction. Thus, tension applied to the tether between the anchor and the tissue graft is automatically maintained by the anchor. After passing through the anchor, the tether may exit the tunnel through the graft site, or through the opposite side of the bone.

12 Claims, 12 Drawing Sheets

(56) References Cited

U.S. PATENT DOCUMENTS

| | | |
|---|---|---|
| 4,480,357 A | 11/1984 | Cummins |
| 4,480,358 A | 11/1984 | Barling et al. |
| 4,502,161 A | 3/1985 | Wall |
| 4,627,853 A | 12/1986 | Campbell et al. |
| 4,646,394 A | 3/1987 | Krauss |
| 4,673,407 A | 6/1987 | Martin |
| 4,773,910 A | 9/1988 | Chen et al. |
| 4,785,509 A | 11/1988 | Fisher |
| 4,831,692 A | 5/1989 | Chuan |
| 4,910,934 A | 3/1990 | Hennings |
| 4,927,421 A | 5/1990 | Goble et al. |
| 4,932,962 A | 6/1990 | Yoon et al. |
| 4,950,270 A | 8/1990 | Bowman et al. |
| 4,976,013 A | 12/1990 | Wax |
| 5,035,699 A | 7/1991 | Coates |
| 5,037,439 A | 8/1991 | Albrektsson et al. |
| 5,067,964 A | 11/1991 | Richmond et al. |
| 5,074,874 A | 12/1991 | Yoon et al. |
| 5,092,895 A | 3/1992 | Albrektsson et al. |
| 5,100,409 A | 3/1992 | Coates et al. |
| 5,123,913 A | 6/1992 | Wilk et al. |
| 5,176,684 A | 1/1993 | Ferrante et al. |
| 5,284,485 A | 2/1994 | Kammerer et al. |
| 5,403,330 A | 4/1995 | Tuason |
| 5,445,167 A | 8/1995 | Yoon et al. |
| 5,456,721 A | 10/1995 | Legrand |
| 5,489,311 A | 2/1996 | Cipolletti |
| 5,527,341 A | 6/1996 | Gogolewski et al. |
| 5,569,259 A | 10/1996 | Ferrante et al. |
| 5,572,770 A * | 11/1996 | Boden .................. 24/136 R |
| 5,584,835 A | 12/1996 | Greenfield |
| 5,593,411 A | 1/1997 | Stalcup et al. |
| 5,601,557 A | 2/1997 | Hayhurst |
| 5,630,824 A | 5/1997 | Hart |
| 5,632,745 A | 5/1997 | Schwartz |
| 5,653,719 A | 8/1997 | Raiken |
| 5,674,224 A | 10/1997 | Howell et al. |
| 5,688,284 A | 11/1997 | Chervitz et al. |
| 5,693,060 A | 12/1997 | Martin |
| 5,725,556 A | 3/1998 | Moser et al. |
| 5,741,281 A | 4/1998 | Martin |
| 5,741,301 A | 4/1998 | Pagedas |
| 5,743,915 A | 4/1998 | Bertin et al. |
| 5,752,964 A | 5/1998 | Mericle |
| 5,759,189 A | 6/1998 | Ferragamo et al. |
| 5,766,250 A | 6/1998 | Chervitz et al. |
| 5,766,255 A | 6/1998 | Slamin et al. |
| 5,769,894 A | 6/1998 | Ferragamo |
| 5,769,899 A | 6/1998 | Schwartz et al. |
| 5,776,201 A | 7/1998 | Colleran et al. |
| 5,782,864 A | 7/1998 | Lizardi |
| 5,839,768 A | 11/1998 | Wackerly |
| 5,860,981 A | 1/1999 | Bertin et al. |
| 5,879,391 A | 3/1999 | Slamin |
| 5,891,168 A | 4/1999 | Thal |
| 5,921,986 A * | 7/1999 | Bonutti .................. 606/60 |
| 5,931,855 A | 8/1999 | Buncke |
| 5,950,284 A | 9/1999 | Persson |
| 6,024,758 A | 2/2000 | Thal |
| 6,030,007 A | 2/2000 | Bassily et al. |
| 6,045,574 A | 4/2000 | Thal |
| 6,056,752 A | 5/2000 | Roger |
| 6,066,160 A * | 5/2000 | Colvin et al. .................. 606/232 |
| 6,066,173 A | 5/2000 | McKernan et al. |
| 6,068,648 A | 5/2000 | Cole et al. |
| 6,071,311 A | 6/2000 | O'Neil et al. |
| 6,095,282 A | 8/2000 | Sadeck |
| 6,099,568 A | 8/2000 | Simonian et al. |
| 6,106,545 A | 8/2000 | Egan |
| 6,132,439 A | 10/2000 | Kontos |
| 6,168,629 B1 | 1/2001 | Timoteo |
| 6,171,317 B1 | 1/2001 | Jackson et al. |
| 6,171,342 B1 | 1/2001 | O'Neil et al. |
| 6,235,057 B1 | 5/2001 | Roger et al. |
| 6,283,996 B1 | 9/2001 | Chervitz et al. |
| 6,319,271 B1 | 11/2001 | Schwartz et al. |
| 6,371,958 B1 | 4/2002 | Overaker |
| 6,432,123 B2 | 8/2002 | Schwartz et al. |
| 6,461,373 B2 | 10/2002 | Wyman et al. |
| 6,482,210 B1 | 11/2002 | Skiba |
| 6,485,065 B2 | 11/2002 | Lusk et al. |
| 6,520,964 B2 | 2/2003 | Tallarida et al. |
| 6,544,267 B1 | 4/2003 | Cole et al. |
| 6,554,838 B2 | 4/2003 | McGovern et al. |
| 6,558,389 B2 | 5/2003 | Clark |
| 6,562,071 B2 | 5/2003 | Jarvinen |
| 6,575,986 B2 | 6/2003 | Overaker |
| 6,610,067 B2 | 8/2003 | Tallarida et al. |
| 6,652,561 B1 | 11/2003 | Tran |
| 6,656,183 B2 * | 12/2003 | Colleran et al. .................. 606/232 |
| 6,679,917 B2 | 1/2004 | Ek |
| 6,743,232 B2 | 6/2004 | Overaker et al. |
| 6,749,616 B1 | 6/2004 | Nath |
| 6,751,143 B2 | 6/2004 | Morgan et al. |
| 6,761,722 B2 * | 7/2004 | Cole et al. .................. 606/74 |
| 6,770,076 B2 | 8/2004 | Foerster |
| 2002/0055783 A1 | 5/2002 | Tallarida et al. |
| 2002/0120274 A1 | 8/2002 | Overaker et al. |
| 2002/0120281 A1 | 8/2002 | Overaker |
| 2002/0123758 A1 | 9/2002 | Bachman et al. |
| 2002/0138150 A1 | 9/2002 | Leclercq |
| 2002/0147498 A1 | 10/2002 | Tallarida et al. |
| 2003/0060887 A1 | 3/2003 | Ek |
| 2003/0120276 A1 | 6/2003 | Tallarida et al. |
| 2003/0158606 A1 | 8/2003 | Coon et al. |
| 2003/0225456 A1 | 12/2003 | Ek |
| 2003/0225457 A1 | 12/2003 | Justin et al. |
| 2004/0015170 A1 | 1/2004 | Tallarida et al. |
| 2004/0098053 A1 | 5/2004 | Tran |
| 2004/0133217 A1 | 7/2004 | Watschke |
| 2004/0133238 A1 | 7/2004 | Cerier |
| 2004/0133239 A1 * | 7/2004 | Singhatat .................. 606/232 |
| 2004/0138683 A1 | 7/2004 | Shelton et al. |
| 2004/0138706 A1 | 7/2004 | Abrams et al. |
| 2004/0148030 A1 | 7/2004 | Ek |
| 2004/0153103 A1 | 8/2004 | Schwartz et al. |
| 2006/0122608 A1 * | 6/2006 | Fallin et al. .................. 606/72 |

FOREIGN PATENT DOCUMENTS

| | | |
|---|---|---|
| WO | WO8909578 A1 | 10/1989 |
| WO | WO0166021 A1 | 9/2001 |
| WO | WO0166022 A1 | 9/2001 |
| WO | WO03051210 A2 | 6/2003 |
| WO | WO03051211 A1 | 6/2003 |
| WO | WO2004062506 A1 | 7/2004 |

* cited by examiner

LINE LOCK GRAFT RETENTION SYSTEM AND METHOD

CROSS-REFERENCE TO RELATED APPLICATIONS

This application is a continuation of U.S. application Ser. No. 11/112,814, filed Apr. 21, 2005, and is entitled LINE LOCK GRAFT RETENTION SYSTEM which is a continuation-in-part of U.S. application Ser. No. 11/030,462, filed Jan. 6, 2005, and is entitled TRANSOSSEOUS GRAFT RETENTION SYSTEM AND METHOD. The foregoing are incorporated herein by reference.

The following disclosures are also incorporated herein by reference:

U.S. application Ser. No. 10/459,375, filed Jun. 11, 2003, is entitled LINE LOCK SUTURE ATTACHMENT SYSTEMS AND METHODS;

U.S. application Ser. No. 10/936,376, filed Sep. 7, 2004, is entitled ADJUSTABLE LINE LOCKS AND METHODS;

U.S. application Ser. No. 10/942,275, filed Sep. 15, 2004, is entitled LINE LOCK THREADING SYSTEMS AND METHODS;

U.S. application Ser. No. 11/001,866, filed Dec. 1, 2004, is entitled LINE LOCK SUTURE ATTACHMENT SYSTEMS AND METHODS;

U.S. application Ser. No. 09/970,559, filed Oct. 3, 2001, is entitled METHOD AND APPARATUS FOR RECONSTRUCTING A LIGAMENT;

U.S. application Ser. No. 10/798,665, filed Mar. 11, 2004, is entitled IMPLANTS AND RELATED METHODS AND APPARATUS FOR SECURING AN IMPLANT ON AN ARTICULATING SURFACE OF AN ORTHOPEDIC JOINT; and U.S. application Ser. No. 10/901,941, filed Jul. 28, 2004, is entitled TETHERED JOINT BEARING IMPLANTS AND SYSTEMS.

BACKGROUND OF THE INVENTION

1. The Field of the Invention

The present invention relates generally to restoration of surfaces of articulating joints of the body, and more specifically, to restoration of a surface formed of articular cartilage through the use of a tissue graft.

2. The Relevant Technology

The articulating surfaces of various joints of the body, such as the adjacent surfaces of the tibia and femur, are covered with cartilage that facilitates relative sliding. Due to trauma, disease, or wear, local defects can be formed in such surfaces. Such defects can cause discomfort for a patient and accelerate wear of the remaining cartilage.

Accordingly, several treatments have been developed to address problems with cartilage articulation surfaces. According to one known treatment, a cartilage graft is harvested from some other part of the body (thereby providing an "autograft"), and is positioned at the site of the defect. Via various methods known in the art, graft incorporation may be promoted to help integrate the graft with the surrounding cartilage.

Unfortunately, keeping the cartilage graft in place presents a somewhat unique challenge. According to some known methods, the graft may be fastened to the graft site, or held within a cage attached to the bone behind the articulation surface. Unfortunately, many such retention mechanisms inhibit contact and/or fluid flow between the graft and the surrounding cartilage, thereby inhibiting incorporation. Additionally, some such mechanisms leave components in the body that will not be absorbed by the body, and thus have the potential to become dislodged and damage the articulation surfaces. Further, some such mechanisms are complex and/or difficult to implant in the body, thereby increasing the expense of the operation, the invasiveness of the surgery, the healing time required, and the probability of failure.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
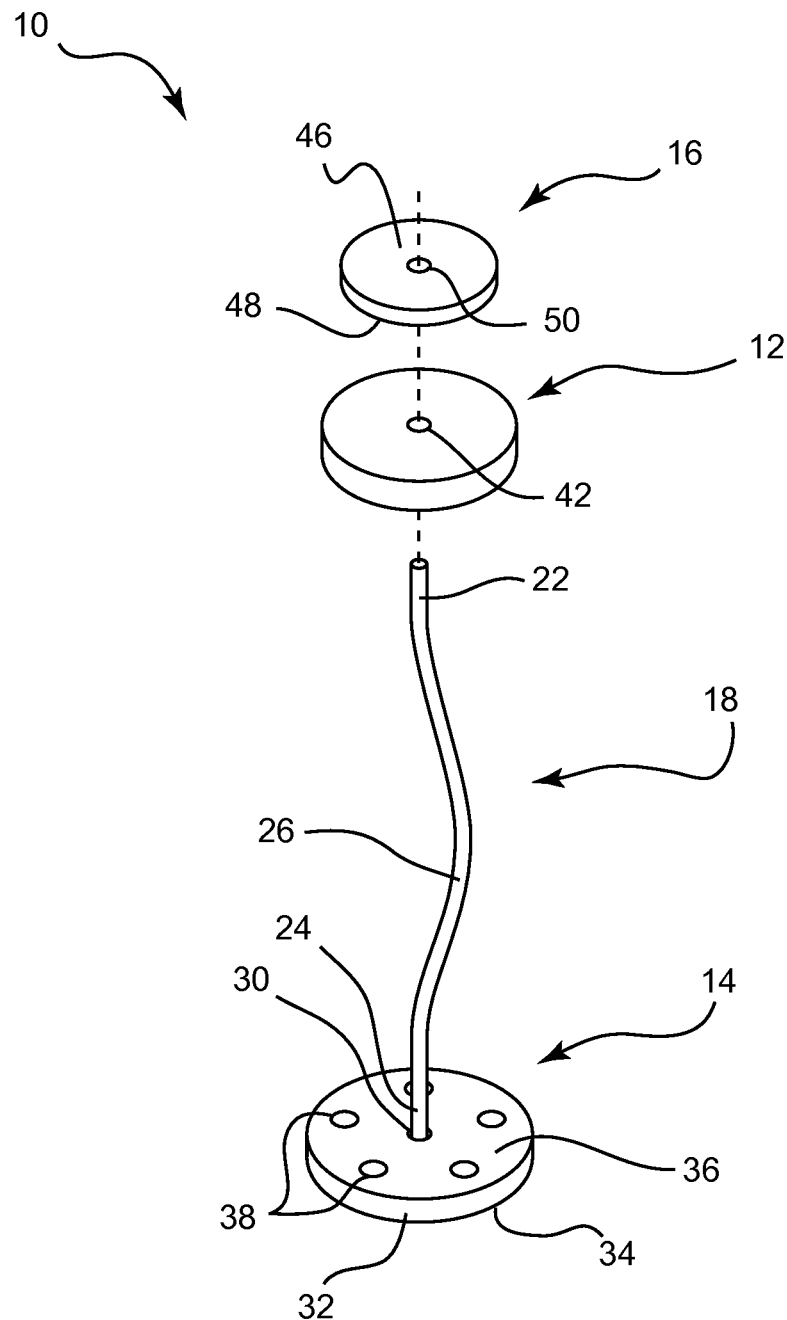
FIG. 1 is an exploded, perspective view of a system for articulation surface repair according to one embodiment of the invention.

The present invention relates to tissue grafts for restoration of cartilage articulation surfaces, including, but not limited to, articulation surfaces of the knee. Those of skill in the art will recognize that the systems and methods described herein may be readily adapted for restoration of other types of tissue, or other types of articulation surfaces.

In this application, a "tunnel" refers to any type of man-made passageway passing partially or completely through a bone. To "capture" a first object with a second object refers to application of pressure on at least one surface of the first object with the second object to keep the first object generally in place. Some relative motion between the two objects may be permitted. Capturing does not require that the second object completely contain or enclose the first object. "Actuation" refers to any type of motion or deformation of an object or of a portion thereof. Thus, a portion of a suture may be "actuated" to form a knot in the suture.

A "flexible member" is a member designed to undergo large deflections, such as a suture, cable, wire, or the like. The term "direction," when used in connection with motion of a flexible member such as a line, does not necessarily refer to a static vector. Rather, a "direction" may refer to motion of the line along a pathway, toward one specified end of the pathway. Thus, stating that a line is only able to move along a pathway in one direction means that the line can only be advanced toward one end of the pathway. The line moves along the pathway in one direction even though in the course of advancement along the pathway, segments of the line will simultaneously be moving along a variety of differently-oriented vectors.

A "tether" refers to a member capable of linking two objects to restrict motion of the objects away from each other. A tether need not be a flexible member, but may instead be a rigid link. "Incorporation" of a graft tissue with a graft site does not require that the graft tissue and the graft site become homogeneous; rather, it simply means that linking material is provided in intervening space between the graft tissue and the graft site to bring the exposed surfaces of the graft site and the graft tissue closer to a continuous, smooth shape. To "couple" two objects together does not require that relative motion between the objects is entirely prevented, but rather that the motion of one of the objects is in some way linked to motion of the other.

A first object that "substantially encircles" a second object need not extend a full 360° around the second object. Rather, the first object extends more than 180° around the second object. The term "attach" is broadly interpreted to include securement of separate elements to each other, and the integral formation of separate elements with each other. Thus, two portions of an object that are unitarily formed in a single operation may be said to be "attached" together. Furthermore, two objects are attached together if their relationship is such that relative motion between the objects is restricted in at least one direction. Attachment does not require impediment of relative motion in all directions. The term "lock" also does not require restriction of relative motion in all directions.

Referring to FIG. 1, a perspective view illustrates a graft system according to one embodiment of the invention. As shown, the system 10 has a tissue graft 12 that is designed to be positioned at a graft site (not shown in FIG. 1), which may be a region of articular cartilage in which some of the cartilage is missing due to wear or trauma. The tissue graft 12 may be a piece of cartilage harvested from some other part of the patient's body (an autograft) or from a compatible human donor (an allograft), or from an animal donor (a xenograft). Alternatively, the tissue graft 12 may be artificially formulated (a synthetic graft). The system 10 also has a cover 14, an anchor 16, and a tether in the form of a suture 18. The cover 14, anchor 16, and suture 18 cooperate to keep the tissue graft 12 in place with respect to the graft site.

As shown, the suture 18 has a first end 22 and a second end 24. The second end 24 may initially be attached to the cover 14, and the first end 22 may subsequently be coupled to the anchor 16 in such a manner that the cover 14 is held in place to capture the tissue graft 12 with respect to the graft site, as will be shown and described subsequently in greater detail. The suture 18 also has an intermediate portion 26 between the first end 22 and the second end 24.

The cover 14 has a socket 30 within which the second end 24 of the suture 18 is retained in a substantially permanent manner. The cover 14 also has a periphery 32, an outer surface 34, and a retention surface 36. The outer surface 34 faces outward with respect to the tissue graft 12, and the retention surface 36 faces inward, toward the tissue graft 12. Some part of the retention surface 36 may abut the tissue graft 12 when the system 12 is installed to effectively capture the tissue graft 12.

Optionally, the periphery 32 of the cover 14 may be larger than the tissue graft 12, so that the cover 14 cooperates with the graft site (not shown) to substantially enclose the tissue graft 12. The cover 14 has a generally fluid-permeable structure that permits relatively easy passage of fluids such as synovial fluid and other body fluids, proteins, growth factors, and the like to the tissue graft 12 to simulate regeneration of the articular cartilage or incorporation of the tissue graft 12 into the surrounding articular cartilage. Thus, the cover has a plurality of holes 38 extending from the outer surface 34 to the retention surface 36. In alternative embodiments of the invention, a cover may be sized smaller than a tissue graft to provide retention, but not enclosure, of the tissue graft. A perforated structure may or may not be desirable for such a smaller cover.

The cover 14 may also be bioabsorbable so that, over time, the cover 14 can be absorbed by the body without adversely affecting the operation of joints or other biological systems. The perforated structure of the cover 14 helps to increase the surface area-to-volume ratio of the cover 14, thereby increasing the rate at which the cover 14 is absorbed by the patient's body. The rate of absorption may be tuned to ensure that the necessary incorporation and/or regeneration of the graft site is able to occur before the cover 14 loses its ability to keep the tissue graft 12 in place.

A wide variety of bioabsorbable materials may be used to form the cover 14. Examples of suitable materials include homopolymers and copolymers of lactide, glycolide, trimethylene carbonate, caprolactone, and p-dioxanone and blends or other combinations thereof and equivalents thereof. Examples of non-absorbable homopolymers and copolymers materials include non-absorbable polyesters, polyorthoesters, polyanhydrides, polycarbonates, polyurethanes, polyamides and polyalkylene oxides, polyolefins, and polyacetals and equivalents thereof. Bioactive and absorbable glasses or ceramics comprising calcium phosphates and other biocompatible metal oxides (i.e., CaO) may also be used.

The tissue graft 12 may have a disc-like shape, as shown, or any other shape. Different shapes and sizes may be selected to suit a variety of graft site shapes. The tissue graft 12 has a central opening 42 through which the suture 18 is able to pass.

The shape of the cover 14 may be matched to that of the tissue graft 12. Thus, in the system 10 of FIG. 1, the cover 14 has a disc-like shape that corresponds to the disc-like shape of the tissue graft 12. The cover 14 may also be contoured in three dimensions to define a substantially continuous contour in combination with the surrounding natural cartilage. Thus, the edges of the cover 14 do not protrude with respect to the surrounding cartilage when the cover 14 is installed. Accordingly, the cover 14 does not significantly abrade the articular surface that articulates against the cover 14.

The anchor 16 may also have a disc-like shape. The anchor 16 is designed to retain the first end 22 of the suture 18 via knotting or other methods, as will be discussed subsequently. The anchor 16 may have an outer surface 46 that faces generally outward with respect to the tissue graft 12, and the retention surface 48 faces generally inward, toward the tissue graft 12. The anchor 16 also has a central opening 50 that extends from the outer surface 46 to the retention surface 48. The central opening 50 is sized to permit passage of the suture 18 therethrough to facilitate retention of the first end 22.

Optionally, the anchor 16 may also be bioabsorbable. The rate of absorption of the anchor 16 may be tuned to ensure that the necessary incorporation and/or regeneration of the graft site is able to occur before the anchor 16 loses its ability to keep the first end 22 in place.

The cover 14, anchor 16, and suture 18 are relatively easily installed using procedures that are less invasive than many known graft placement procedures. Furthermore, the tissue graft 12 can be securely retained in a manner that does not inhibit tissue incorporation or regeneration. The manner in which the system 10 is installed will be set forth in greater detail in the following description of FIGS. 2 through 5.

Figure 2:
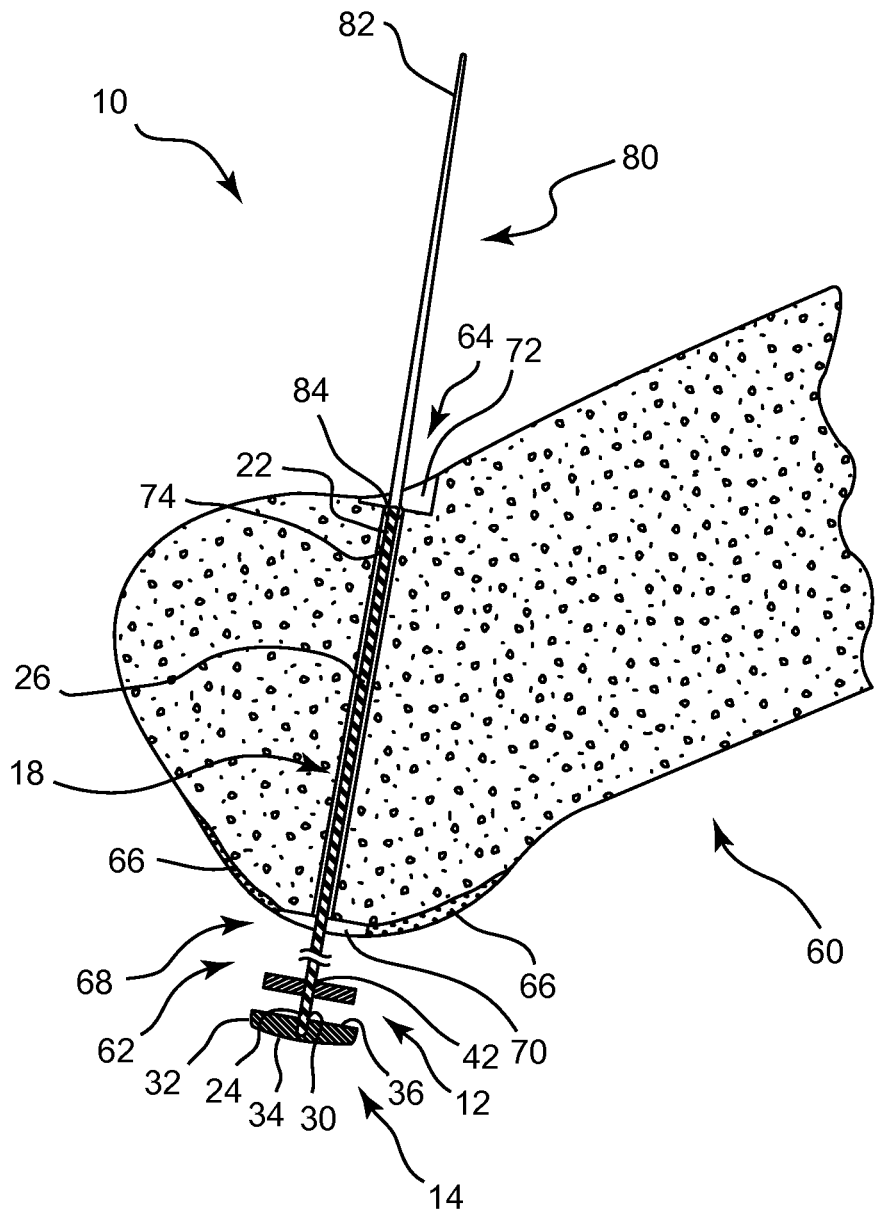
FIG. 2 is a side elevation, section view of a femur with a tunnel formed therein to receive the system of FIG. 1, with the suture inserted through the tissue graft and partially through the tunnel.

Referring to FIG. 2, a side elevation, section view illustrates an initial step in the installation of the system 10 in a patient, or more specifically, in a part of a joint such as the knee. More precisely, FIG. 2 illustrates the end of a bone 60, which may be a patient's femur. The bone 60 has a graft side 62 to which the tissue graft 12 is to be applied, and an anchoring side 64 to which the anchor 16 is to be coupled. The graft side 62 has articular cartilage 66 that forms a smooth surface along which a corresponding articular surface of the tibia is easily slidable.

The graft side 62 also has a graft site 68, which is the defect in the articular cartilage 66 that is to be repaired through the use of the tissue graft 12. Thus, the graft site 68 may have a cavity 70, which may have a shape defined by the particular wear or trauma that necessitated the use of the graft operation. Alternatively, reaming or other operations may be performed at the graft site 68 to remove degenerative tissue and/or provide the cavity 70 with a shape conducive to rapid incorporation and/or regeneration of the tissue graft 12. For example, prior to installation of the tissue graft 12, the cavity 70 may be shaped to match the shape of the cavity 70 to the tissue graft 12.

As shown, the anchoring side 64 also has a cavity 72, which may be reamed or otherwise formed in a manner that facilitates retention of the anchor 16 therein, as will be described subsequently. A tunnel 74 is formed, for example, via drilling, to provide communication between the graft side 62 and the anchoring side 64. The tunnel 74 may have a generally circular cross sectional shape, and may extend from the cavity 70 of the graft site 68 to the cavity 72 of the anchoring side 64.

Initially, the graft site 62 may be exposed by cutting open the skin and spreading any muscle tissue and tendons that cover the graft site 68. The cavity 70 may then be shaped as desired. The anchoring side 64 need not necessarily be exposed at this stage, but may optionally be exposed to facilitate shaping of the cavity 72.

Once the graft site 62 has been prepared, the first end 22 of the suture 18 may be inserted through the central opening 42 of the tissue graft 12. The first end 22 may then be advanced through the tunnel 74 through the use of a needle 80. As shown, the needle 80 has a tip 82 with a sharpened shape, and an eyelet 84. The first end 22 may be secured to the needle 80 by inserting it through the eyelet 84 and, for example, tying it with a conventional knot.

Once the first end 22 has been secured to the needle 80, the tip 82 of the needle 80 may be inserted through the cavity 70 of the graft side 62 and into the tunnel 74. The needle 80 may be pushed through the tunnel 74 until the tip 82 exits the tunnel 74 on the anchoring side 64 of the bone 60. The needle 80 may be further actuated to draw the first end 22 through the tunnel 74 and out of the tunnel 74 at the anchoring side 64. If the anchoring side 64 has not yet been exposed, this may entail pushing the tip 82 through the skin covering the anchoring side 64. If desired, the needle 80 may be longer than is illustrated in FIG. 2 to ensure that a portion of the needle 80 is always exposed and easily actuated during performance of the above-described process.

Figure 3:
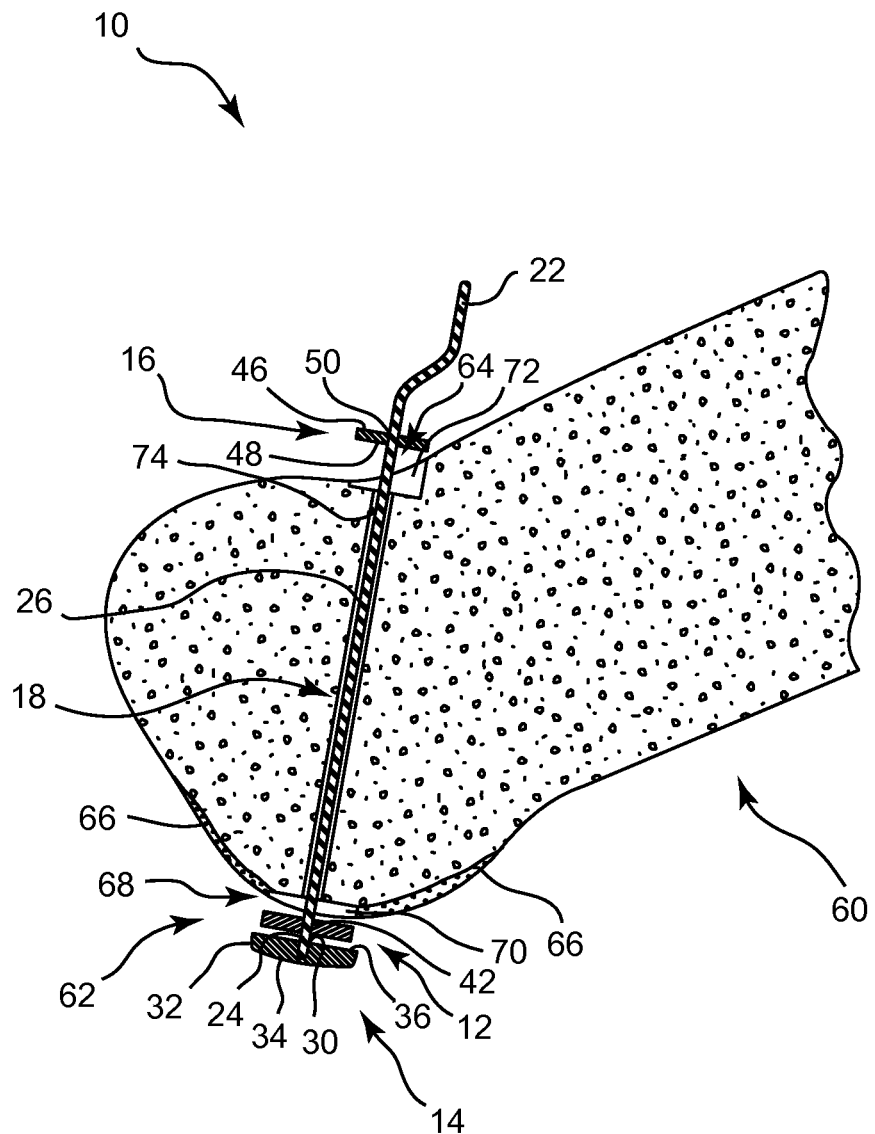
FIG. 3 is a side elevation, section view of the femur and the system of FIG. 1, in which the suture is fully drawn through the tunnel and through the corresponding anchor.

Referring to FIG. 3, a side elevation, section view illustrates another step in the installation of the system 10 in the patient. As shown, the first end 22 has passed fully through the tunnel 74 to position the second end 24, the cover 14, and the tissue graft 12 proximate the graft site 68. The needle 80 has been removed from the first end 22, for example, by untying or cutting away the knot by which the first end 22 was attached to the eyelet 84.

Furthermore, the first end 22 has also been inserted through the anchor 16. More precisely, the first end 22 has been inserted through the central opening 50 of the anchor 16 to pass from the retention surface 48 to the outer surface 46. The anchor 16 has been further actuated along the suture 18 until it rests within the cavity 72 of the anchoring side 64. The anchor 16 is sized to fit into the cavity 72, but not into the tunnel 74. Thus, the cavity 72 defines a shoulder on which the anchor 16 is able to rest due to abutment of the retention surface 48 against the shoulder.

Figure 4:
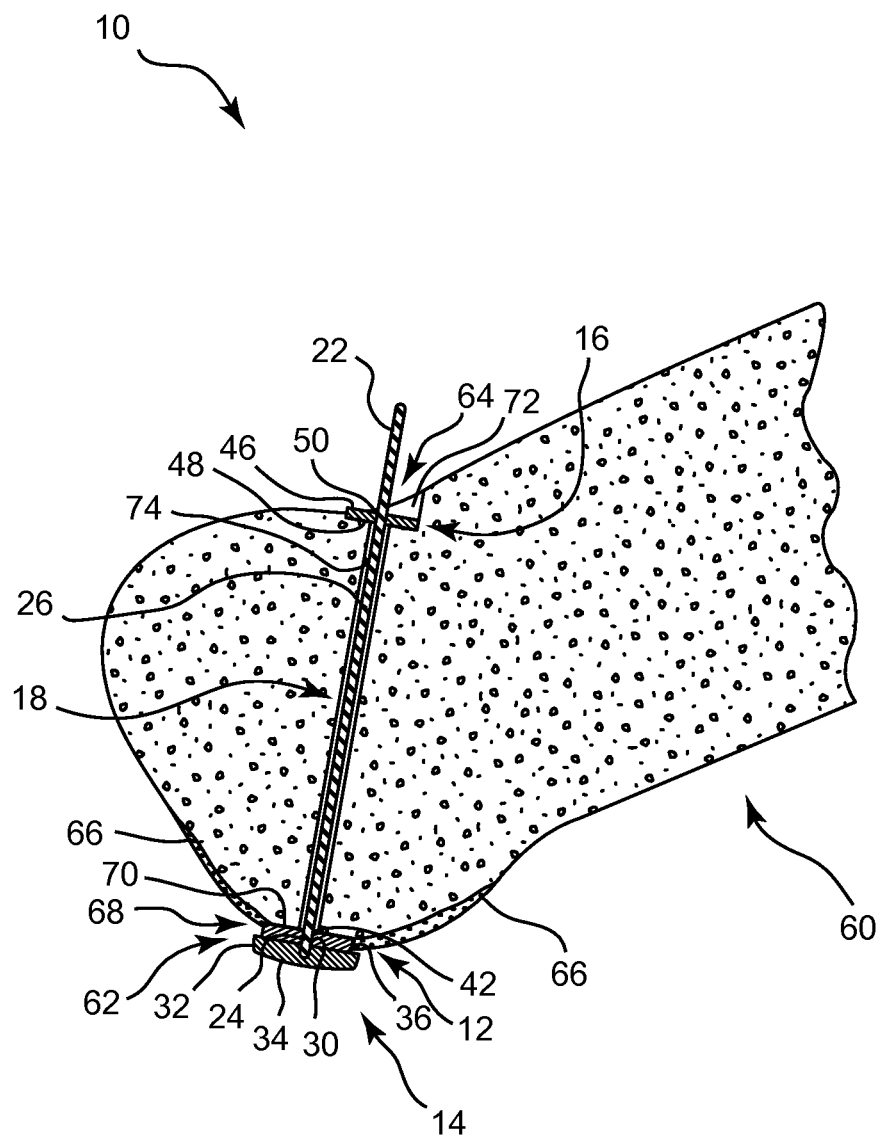
FIG. 4 is a side elevation, section view of the femur and the system of FIG. 1, in which the suture is tightened to urge the tissue graft toward the graft site via the cover.

Referring to FIG. 4, a side elevation, section view illustrates another step in the installation of the system 10 in the patient. The suture 26 has been further drawn through the central opening 50 of the anchor 16 to draw the cover 14 against the articular cartilage 66, thereby positioning the tissue graft 12 within the cavity 70 of the graft site 68. The intermediate portion 26 of the suture 18 has been drawn taught within the tunnel 74 so that tension in the intermediate portion 26 holds the cover 14 in place against the articulate cartilage 66, and holds the anchor 16 in place against the shoulder defined by the cavity of the anchoring side 64.

The retention surface 36 of the cover 14 may press directly against the tissue graft 12 to keep it in place by pressing it against the graft site 68. Alternatively, the portion of the retention surface 36 adjacent to the periphery 32 of the cover 14 may rest on the articular cartilage 66 surrounding the graft site 66 to form a space within which the tissue graft 12 has some freedom of movement. Such freedom of movement may enhance fluid access to the tissue graft 12. The tissue graft 12 is still "secured" to the graft site 68 because it is unable to leave the space defined by cooperation of the cover 14 with the graft site 68.

Figure 5:
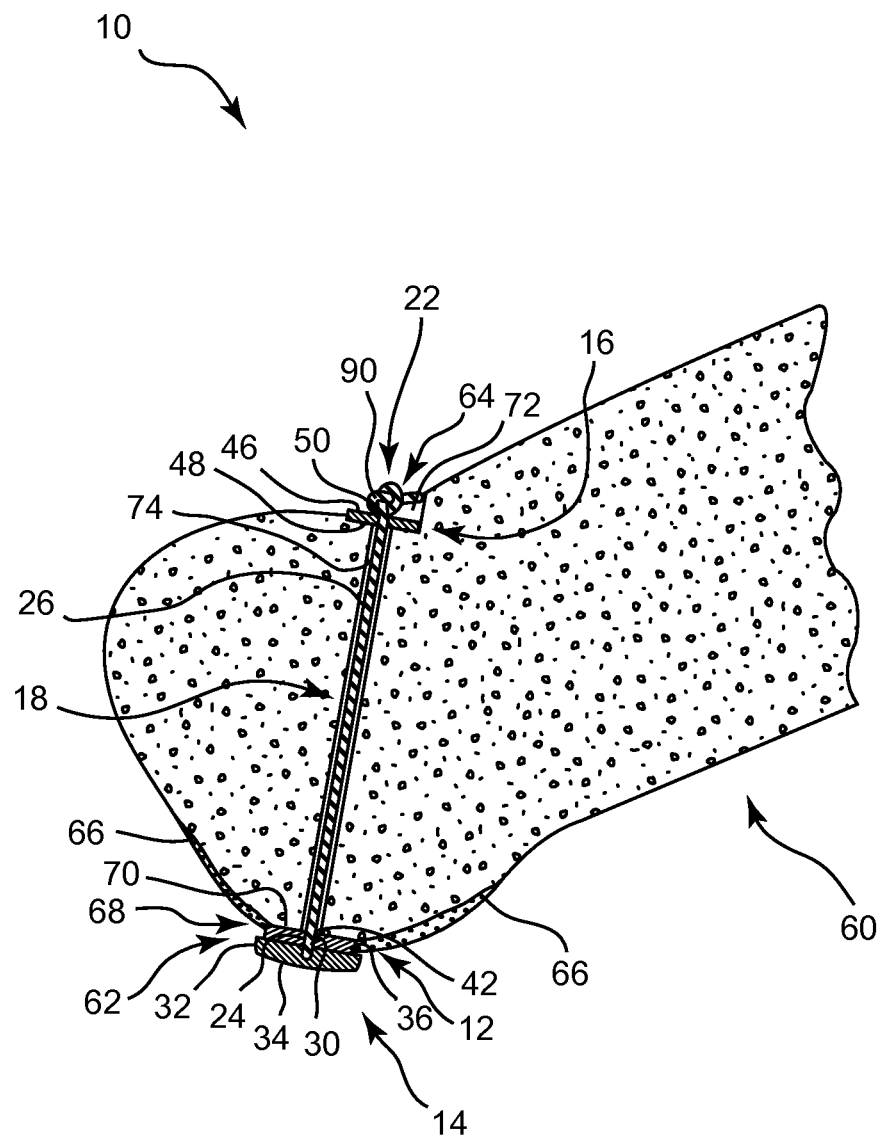
FIG. 5 is a side elevation, section view of the femur and the system of FIG. 1, in which a portion of the suture is locked with respect to the anchor to maintain tension in the suture.

Referring to FIG. 5, a side elevation, section view illustrates yet another step in the installation of the system 10 in the patient. As shown, the suture 26 has been kept taught while a knot 90 has been tied in the first end 22, adjacent to the anchor 16. The knot 90 is too large to pass through the central opening 50 of the anchor 16, and therefore preserves the tension in the intermediate portion 26 of the suture 18. Thus, the cover 14 and the anchor 16 remain in place to keep the tissue graft 12 properly positioned within the graft site 68 while incorporation and/or regeneration take place.

The knot 90 therefore serves as a retention feature that keeps the first end 22 in place proximate the anchoring side 64 of the bone 60, independently of positioning the first end 22 proximate the anchoring side. Thus, unlike a bone screw, the suture 18 is retained in the bone 60 by actuating the first end 22 to form a retention feature, i.e., the knot 90, after positioning of the first end 22 proximate the anchoring side. In the embodiment of FIGS. 1-5, the knot 90 operates in conjunction with the anchor 16 to retain the first end 22. In alternative embodiments, the anchor 16 may be omitted in favor of abutment of the knot 90 directly against the anchoring side 64.

The tissues proximate the graft site 68 and/or the anchoring side 64 of the bone 60 may then be closed, and the healing process may commence. After sufficient incorporation and/or regeneration has occurred, the tissue graft 12 remains in place without the aid of the remainder of the system 10. Accordingly, the cover 14 and/or the anchor 16 may then be absorbed by the body without adversely affecting the healing of the graft site 68.

The principles of the present invention may be applied to a wide variety of embodiments besides that of FIGS. 1-5. For example, in place of the suture 18, an alternative flexible tether (not shown) such as a cable, elastic band, or the like may be used. A flexible barbed line could be ratcheted into a tubular anchor design to receive the barbs. Furthermore, if suture is used, the suture could be braided or monofilament, coated or uncoated, and absorbable or non-absorbable. Such a suture may be formed of natural or synthetic materials, and may be formed of a polymer, a metal, or some combination thereof. An elastomer may even be used. Examples of sutures that may be suitable for the present invention include, but are not limited to VICRYL, coated VICRYL, PDS, catgut, chromic catgut, PROLINE, nylon, ETHIBOND, braided fiberwire, silk, and steel.

Alternatively, a "tether" need not be a flexible line, but may instead be rigid. For example, a cover and an anchor may be tethered together via a rigid rod (not shown) or the like. A rigid rod may have a threaded end that enables the rod to be tensioned and secured with respect to the anchor.

An anchor according to the invention need not be a disc, but may instead have any shape capable of engaging the bone to keep the anchor in place. According to one example, an anchor (not shown) may have an expandable periphery designed to extend outward to engage the wall of the tunnel 74, rather than resting on the shoulder defined by the cavity 72 of the anchoring side 64. An anchor according to the invention therefore need not require that the tunnel 74 extend completely through the bone 60; rather, with some anchor embodiments, a blind hole (not shown) may suffice. An anchor may alternatively have a threaded exterior designed to engage the bone tunnel.

Furthermore, an anchor according to the invention may employ a wide variety of tether retention mechanisms. For example, an anchor may retain a suture by inserting two separate lengths of suture through separate holes of the anchor and then knotting them together, as will be shown and described in connection with FIG. 6. An anchor may alternatively be crimped around a suture to retain the suture, or may have a collet or other gripping device.

As another alternative, an anchor according to the invention may be designed to permit relative motion between the anchor and the suture along only one direction. For example, the anchor may have holes arranged in such a pattern that one or two suture lengths can be inserted therethrough along a pattern that permits motion of the suture along the pattern in only one direction. Alternatively, an anchor (not shown) may have a ball within a conical cavity through which the suture passes; the ball is drawn to impinge against the suture in response to motion of the suture toward the narrow portion of the cavity, but permits relatively free motion of the suture toward the broad portion of the cavity. The foregoing are merely examples; any known one-way locking device may be used within the scope of the present invention to facilitate tensioning and/or retention of a tether by an anchor.

In yet other alternative embodiments, different cover arrangements may be used. According to one alternative embodiment, a flexible cover may be used in place of the cover 14 of FIGS. 1-5. Such an arrangement will be shown and described in connection with FIG. 6.

Figure 6:
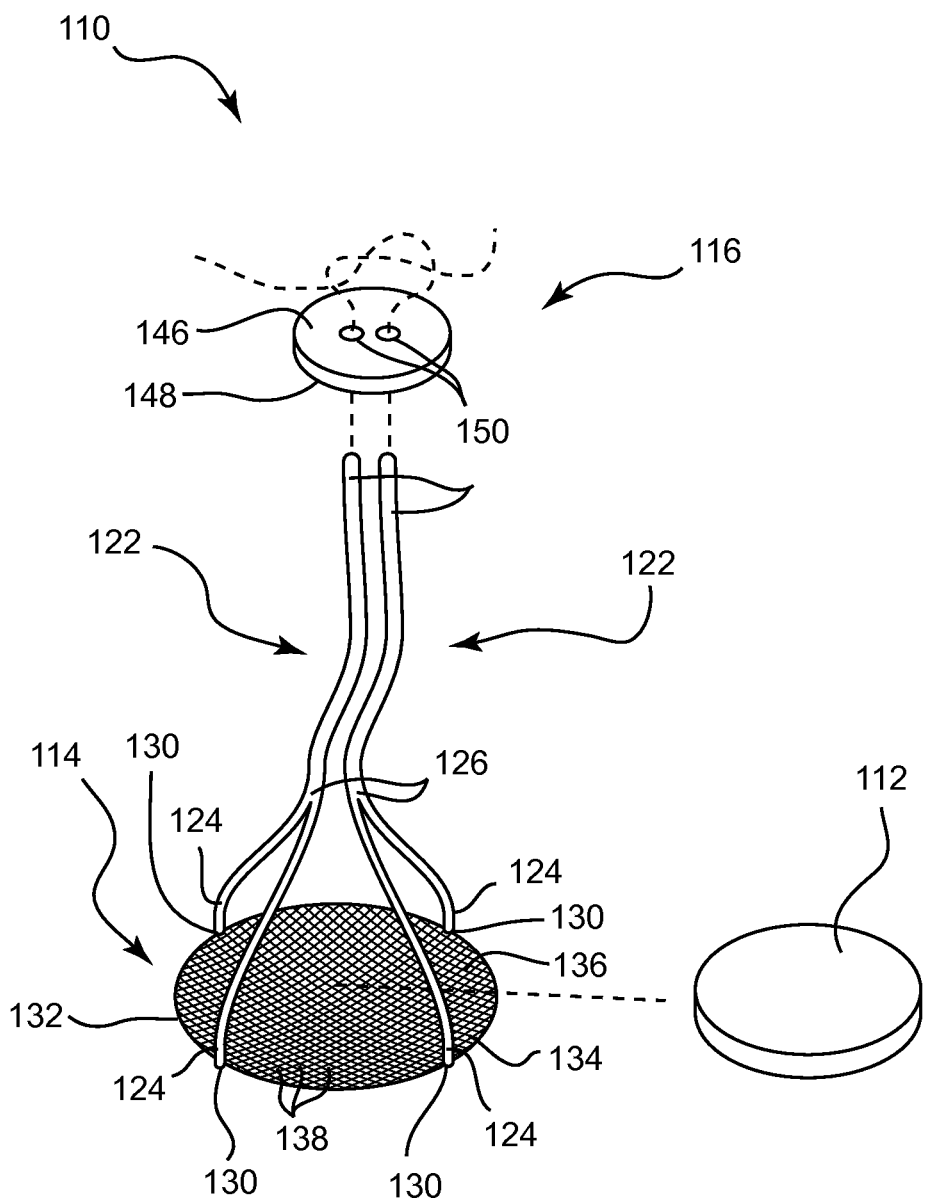
FIG. 6 is an exploded, perspective view of a system for articulation surface repair according to one alternative embodiment of the invention.

Referring to FIG. 6, a perspective view illustrates a graft system 110 according to one alternative embodiment of the invention. As shown, the graft system 110 is designed to retain a tissue graft 112 with respect to a graft site such as the graft site 68 of FIGS. 2 through 5. The graft system 110 has a cover 114, an anchor 116, a first suture 118, and a second suture 120.

Each of the first and second sutures 118, 120 has a first end 122 and two second ends 124, each of which is attached to the cover 114. Further, each of the first and second sutures 118, 120 has an intermediate portion in which a junction 126 is present. At the junction 126 of each of the sutures 128, two separate strands converge from the second ends 124 to provide a single strand that extends to the first end 122.

The cover 114 is formed of a flexible mesh such as a fabric. As in the previous embodiment, the cover 114 has a disc-like shape that corresponds to and is slightly broader than that of the tissue graft 112. The cover 114 has four attachment points 130 at which the second ends 124 of the sutures 118, 120 are attached to the cover 114. The attachment points 130 are distributed relatively uniformly about a periphery 132 of the cover 114 so that the periphery 132 is relatively uniformly drawn by tension on the first and second sutures 118, 120.

As in the previous embodiment, the cover 114 has an outer surface 134 that faces outward with respect to the tissue graft 112, and a retention surface 136 that faces the tissue graft 112 and keeps it in place. The mesh structure of the cover 114 provides an array of voids 138 that serve as passageways through the cover 114 to permit fluids such as synovial fluid and other body fluids, proteins, growth factors, and the like to reach the tissue graft 112 from outside the cover 114. The cover 114 may be bioabsorbable, and may be designed to resist absorption long enough for the graft tissue 112 to become sufficiently incorporated into the articular cartilage 66 to remain in place independently.

Many different materials may be used to form the cover 114. Some biocompatible materials that may be used to form the cover 114 include, but are not limited to, Polyester cloth (Dacron), Polyester sheeting (Mylar), Polyester Felt, Polyester Knit, woven Polyester, Polyester Knitted Velour, PTFE Felt, PTFE Knit, acrylic cloth (Orlon), polyvinyl sponge (Ivalon), polyvinyl cloth (Vinyon-N), polyethylene (PE) mesh, polypropylene (PP, Marlex, Prolene) mesh, polytetrafluoroethylene (PTFE, teflon) mesh, expanded polytetrafluoroethylene (ePTFE, gore-tex) mesh, polyvinylidene fluoride (PVDF) mesh, ethyl vinyl acetate (EVA) mesh, nylon/polyamide mesh, thermoplastic polyurethane (TPU) mesh, polyetheretherketone (PEEK) mesh, composite polymer mesh, tantalum mesh, Nickel-Titanium (nitinol, NiTi) mesh, Titanium (Ti) mesh, stainless steel (SS) mesh, composite metal mesh, and silicone mesh. The foregoing materials are biocompatible, but may not necessarily be bioabsorbable.

Some specific examples of such materials include Cook SURGISIS Soft Tissue Graft, Gore DUALMESH Biomaterial, Gore SEAMGUARD Staple Line Reinforcement Material, Gore MYCROMESH, GORE-TEX ACUSEAL Cardiovascular Patch, Gore PRECLUDE Pericardial Membrane, Gore Subcutaneous Augmentation Material, Gore PRECLUDE MVP Dura Substitute, Gore Collagen Coated Knitted Polyester Graft, GORE-TEX Regenerative Membrane, GORE-TEX Titanium Reinforced Regenerative Membrane, Bard OEM Textiles, Bard COMPOSIX Mesh, Bard VISILEX Mesh, Genzyme Biosurgery SEPRAMESH, POREX Meshes, Textile Development Associates SPUNBOND Fabrics, Boston Scientific OEM Textiles, Boston Scientific HEMASHIELD PLATINUM FINESSE Patch, Boston Scientific TRELEX Natural Mesh, Boston Scientific ADVANTAGE Mesh, Atrium Medical PROLITE Mesh, Tricomed S.A. DALLOP Mesh, Tricomed S.A. DALLOP PP Mesh, Ethicon PROLENE Mesh, Ethicon PROCEED Surgical Mesh, Ethicon ULTRAPRO Mesh, and Ethicon MERSILENE Mesh. Those of skill in the art will recognize that other materials may be used.

Further, a wide variety of materials are both biocompatible and bioabsorbable, and may thus be advantageously used to form the cover 114. Some bioabsorbable materials that may be used to form the cover 114 include, but are not limited to, polyglycolic acid (PGA, Dexon), polyglactin (Vicryl) mesh, collagen matrix mesh (human, bovine, or porcine), carbon fiber mesh, Polylactic acid (PLA) mesh, poly 1-lactic acid (PLLA) mesh, Trimethylene Carbonate (TMC) mesh, polydiaxanone (PDS) mesh, oxidized regenerated cellulose (ORC) fabric, poly DL-lactic-co-glycolic acid (PLGA), tricalcium phosphate (TCP), and hydroxy-apatite (HA).

Some specific examples of such materials include Gore SEAMGUARD Bioabsorbable Staple Line Reinforcement Material, Gore RESOLUT XT Regenerative Bioabsorbable Membrane, Gore RESOLUT ADAPT Regenerative Bioabsorbable Membrane, Gore OSSEOQUEST Regenerative Membrane, Textile Development Associates Absorbable Textiles, Genzyme Biosurgery SEPRAFILM, and Ethicon VICRYL Mesh. Those of skill in the art will recognize that other materials may be used.

The anchor 116 of the system 110 of FIG. 6 is also configured differently from that of the system 10 described previously. The anchor 116 has a disc-like shape with an outer surface 146 that faces outward with respect to the tissue graft 112, and a retention surface 148 that faces the tissue graft 112 and abuts a bony surface such as the shoulder defined by the cavity 72 of FIGS. 2 through 5. Additionally, the anchor 116 has two central openings 150 that extend from the retention surface 148 to the outer surface 146. The first ends 122 of the first and second sutures 118, 120 are able to pass through the central openings 150.

Then, the first ends 122 may be tied together via a simple overhand knot, as indicated by the dashed lines in FIG. 6. Alternatively, any other knot may be used. The knot then serves as a retention feature that keeps the first end 122 in place proximate an anchoring side of a bone, in a manner similar to that of the knot 90 of the previous embodiment. Usage of the first and second sutures 118, 120 in a parallel arrangement contributes to the torsional stability of the system 110.

The system 110 of FIG. 6 may be installed in a patient in a manner similar to that of the system 10. Accordingly, the method described in connection with FIGS. 2 through 5 is largely applicable to the system 110. More particularly, with reference to the bone 60 of FIGS. 2 through 5, the graft site 68 may first be exposed, and then the tunnel 74, and optionally the cavities 70, 72, may be formed. The graft tissue 112 may be positioned to rest on the retention surface 136 of the cover 114. The graft tissue 112 has no central opening, and is instead kept in place via the flexibility of the retention surface 136 and the sutures 118, 120 that partially enclose it.

The sutures 118, 120 may then be attached to a needle, such as the needle 80, and inserted through the tunnel 74. According to one example, one of the first ends 122 of the sutures 118, 120 may be inserted through the eyelet 84 of the needle 80, and the first ends 122 may then be tied together to attach both of the sutures 118, 120 to the needle 80. The needle 80 may be inserted through the tunnel 74 to draw the first ends 122 through the tunnel 74.

The first ends 122 may then be inserted through the central openings 150 of the anchor 116 and the sutures 118, 120 may be tensioned to draw the tissue graft 112 into the cavity 70 of the graft site 68 via the cover 114. The periphery 132 of the cover 114 may then rest against the articular cartilage 66 surrounding the graft site 68 to form a compartment within which the tissue graft 112 is securely retained. Once the first and second sutures 118, 120 have been properly tensioned, the first ends 122 of the sutures 118, 120 may be tied together in the manner shown by the dashed lines to maintain the tension in the sutures 118, 120, thereby keeping the tissue graft 112 in place.

The tissues proximate the graft site 68 and/or the anchoring side 64 of the bone 60 may then be closed, and the healing process may commence. As in the previous embodiment, incorporation and/or regeneration occurs, and the tissue graft 112 remains in place without the aid of the remainder of the system 110. Accordingly, the cover 114 and/or the anchor 116 may then be absorbed by the body without adversely affecting the healing of the graft site 68.

Figure 7:
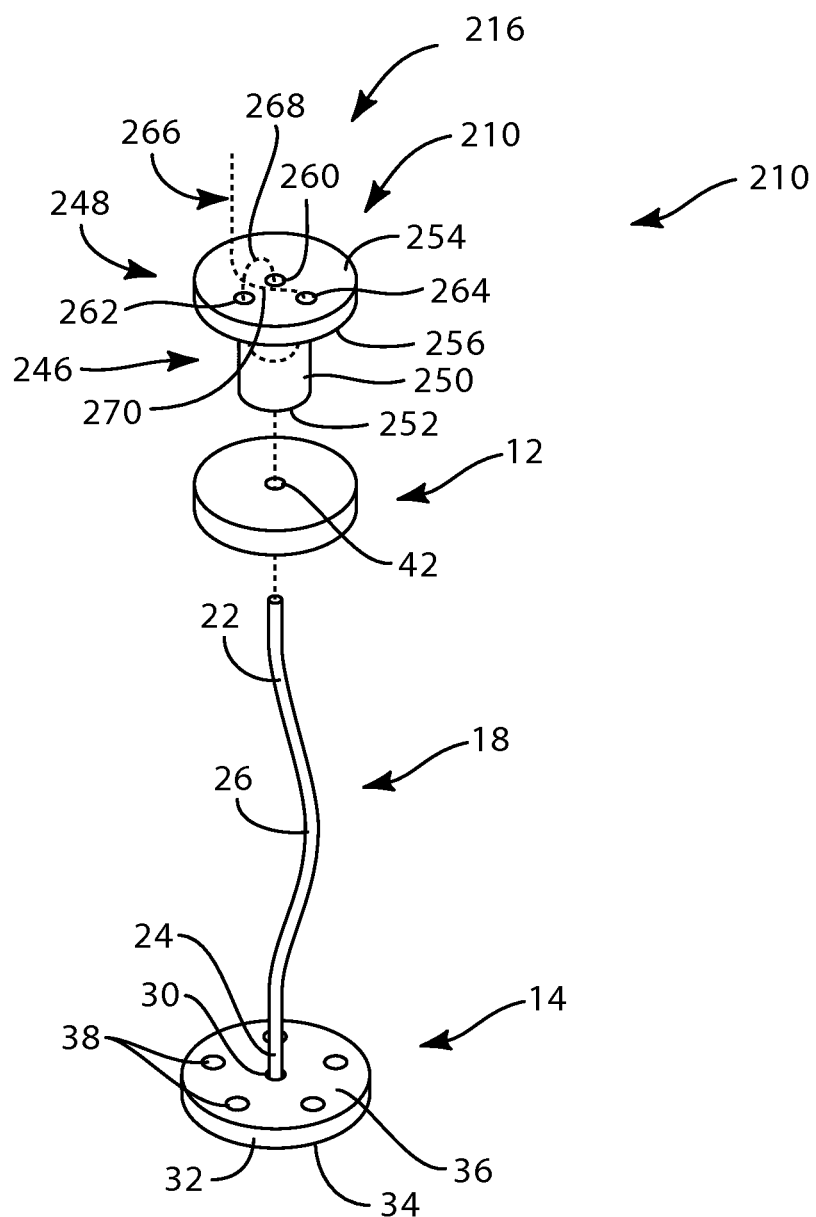
FIG. 7 is an exploded, perspective view of a system for articulation surface repair according to another alternative embodiment of the invention.

Referring to FIG. 7, an exploded, perspective view illustrates a system 210 for articulation surface repair according to another alternative embodiment of the invention. As shown, the system 210 includes a tissue graft 12, a cover 14, and a suture 18, each of which resembles its counterpart in FIGS. 1-5. However, the system 210 has an anchor 216 with a configuration different from that of the anchor 16. The anchor 216 may be termed a "line lock" because it is configured to lock the suture 18 to prevent motion of the suture 18 with respect to the anchor 216 along at least one direction. More precisely, the anchor 216 is designed to permit the suture 18 to pass through it along only one direction, and to lock it to prevent relative motion in the opposite direction.

More precisely, the anchor 216 has a tubular portion 246 and a cap 248. The tubular portion 246 has a generally tubular shape, and the cap 248 is generally disc-shaped, with a diameter large enough to extend beyond the periphery of the tubular portion 246. The tubular portion has an exterior surface 250 and a bore 252 sized to permit the suture 18 to pass relatively freely therethrough. The cap 248 has an outer surface 254 that faces outward, and a retention surface 156 that abuts the corresponding bone surface to keep the anchor 216 in place when the suture 18 is under tension.

The cap 248 also has a first passageway 260, a second passageway 262, and a third passageway 264. The first passageway 260 is in communication with the interior of the tubular portion 246. The second and third passageways 262, 264 do not communicate with the interior of the tubular portion 246; rather, the second and third passageways 262, 264 are located close to the periphery of the cap 248 to communicate with the space surrounding the exterior surface 250 of the tubular portion 246.

The passageways 260, 262, 264 define a pathway 266 along which the first end 22 of the suture 18 can be inserted. As shown, the pathway 266 includes a compression portion 268 and a compressed portion 270. The pathway 266 extends from the first passageway 260 to the second passageway 262 to define the compression portion 268, and then from the third passageway 264 between the compression portion 268 and the outer surface 254 to define the compressed portion 270.

Once the suture 18 has been moved along the pathway 266, tension on the first end 22 of the suture 18 pulls the compression portion 268 away from the outer surface 254 to permit the compressed portion 270 to move, thereby allowing the suture 18 to continue moving along the pathway 266 toward the second end 22. However, tension on the second end 24 of the suture 18 pulls the compression portion 268 toward the outer surface 254 to press the compressed portion 270 securely against the outer surface 254, thereby keeping the suture 18 from moving along the pathway 266 toward the second end 24. If desired, a notch, ridge, or other feature (not shown) may extend along the outer surface 254 between the first and second passageways 260, 262 to enhance locking.

Accordingly, the anchor 216 provides one-way locking by permitting the suture 18 to move through the anchor 216 along one direction, but not in the opposite direction. Locking of the suture 18 by the anchor 216 is "automatic" because the user need not actuate the anchor 216 to activate locking; rather, locking occurs in response to tension tending to pull the suture 18 along the direction for which motion is locked by the anchor 216. In alternative embodiments, an anchor (not shown) according to the invention may be designed to lock a suture in response to some form of deliberate user actuation to prevent relative motion between the anchor and the suture in one or both directions.

Figure 8:
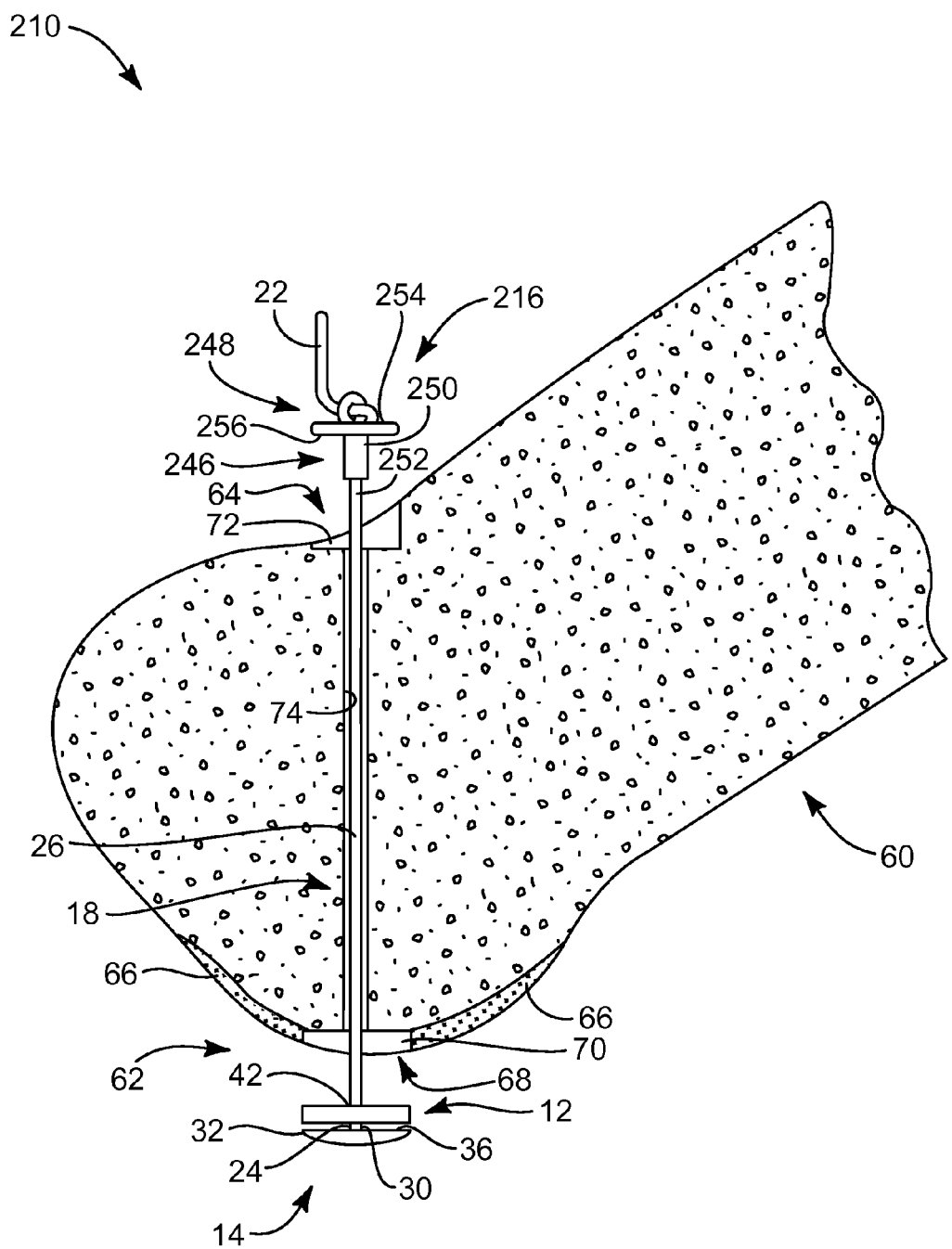
FIG. 8 is a side elevation, section view of a femur with a tunnel formed therein to receive the system of FIG. 7, in which the suture is fully drawn through the tunnel and routed through the passageways through the anchor.

Referring to FIG. 8, a side elevation, partially sectioned view illustrates a bone 60 like that of FIGS. 2 through 5, with the system 210 in the process of being installed in the bone 60 to retain the tissue graft 12. In FIG. 8, the bone 60 has been sectioned, but the system 210 has not bee sectioned. The first end 22 of the suture 18 has been inserted through the central opening 42 of the tissue graft 12, and then through a bore 74 of the bone 60. The first end 22 may be inserted through the bore 74 through the use of a needle such as the needle 80 illustrated in FIG. 2. The needle 80 is then removed, and the first end 22 is inserted through the anchor 216 along the pathway 266 shown in FIG. 7.

Figure 9:
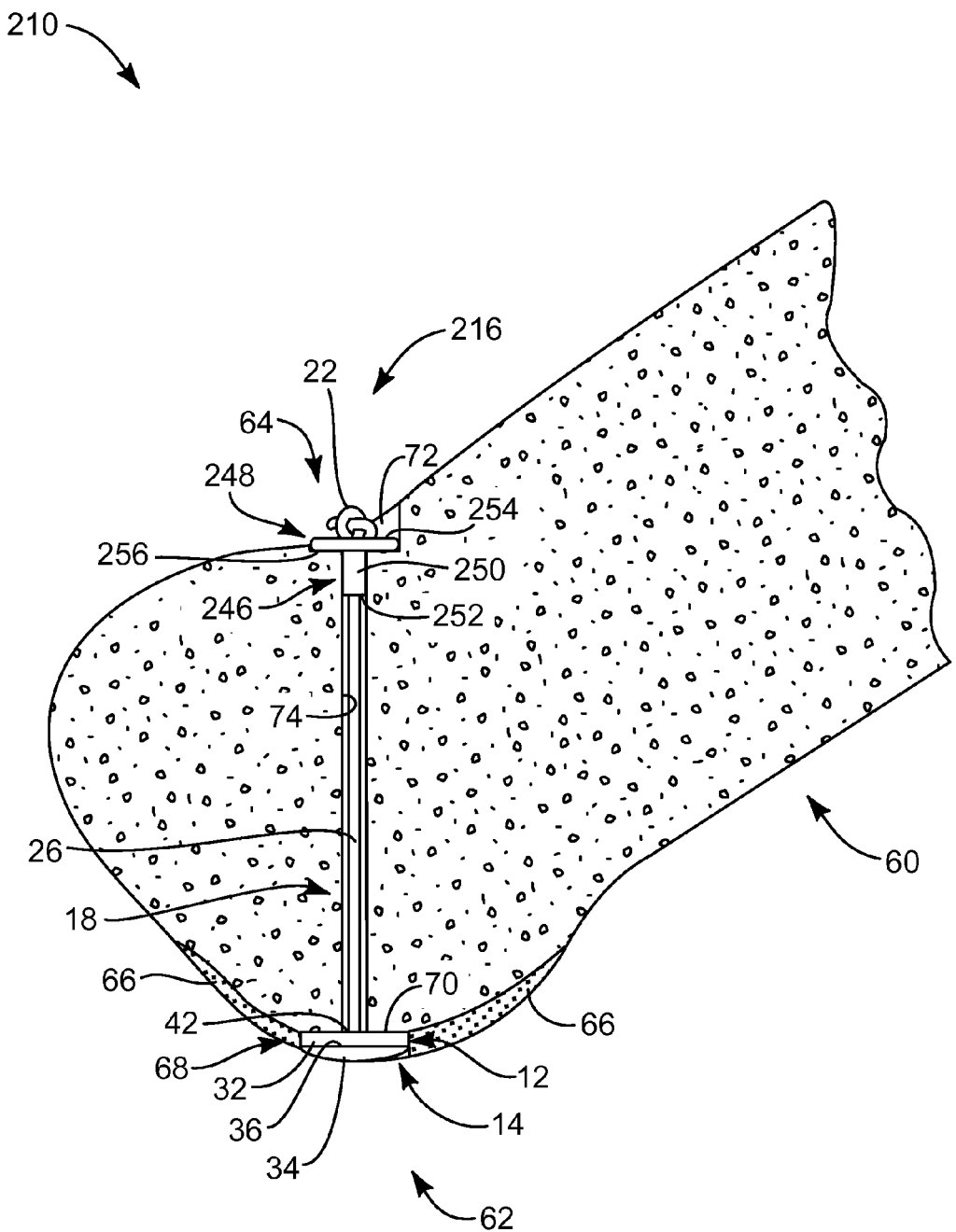
FIG. 9 is a side elevation, section view of the femur and the system of FIG. 7, in which the cover has been cinched against the graft site to retain the tissue graft, with the suture locked with respect to the anchor to maintain tension in the suture.

Referring to FIG. 9, a side elevation, partially sectioned view illustrates the bone 60 of FIG. 8, with the system fully installed in the bone 60 to retain the tissue graft 12. Again, the bone 60 has been sectioned, but the system 210 has not been sectioned. From the configuration of FIG. 8, the first end 22 may be drawn with respect to the anchor 216 to urge continued motion of the suture 18 along the pathway 266, toward the first end 22. As mentioned previously, motion of the suture 18 along this direction may freely occur, while motion along the pathway 266 toward the second end 24 is prohibited. The anchor 216 slides into the anchoring side 64 of the bone 60 such that the tubular portion 246 enters the bore 74, and the cap 248 is positioned within the cavity 72.

The suture 18 may be drawn along the pathway 266 until the intermediate portion 26 of the suture 18 is taught within the bore 74. The retention surface 256 of the cap 248 then abuts the shoulder defined by the transition between the bore 74 and the cavity 72 to maintain the tension by keeping the anchor 216 from moving further into the bore 74. Thus, the tissue graft 12 is sandwiched securely between the cover 14 and the graft site 68. The first end 22 of the suture 18 may be cut to remove the excess portion of the suture adjacent to the compressed portion 270 of the pathway 266.

Figure 10:
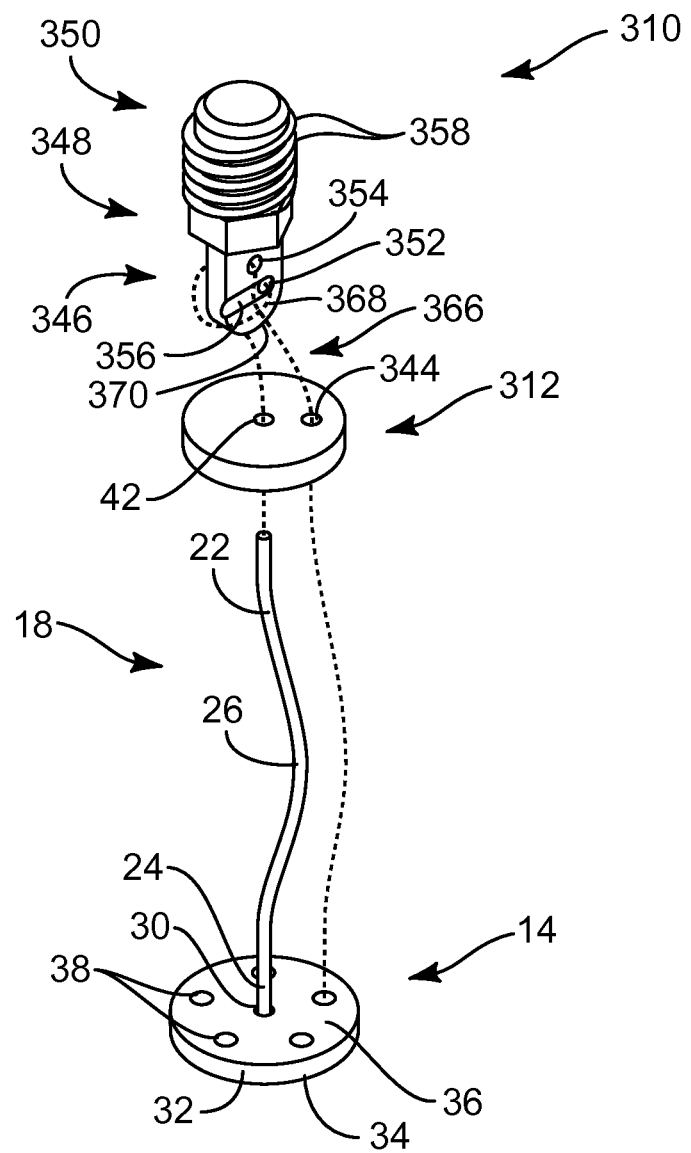
FIG. 10 is an exploded, perspective view of a system for articulation surface repair according to yet another alternative embodiment of the invention.

Referring to FIG. 10, an exploded, perspective view illustrates a system 310 for articulation surface repair according to yet another alternative embodiment of the invention. As shown, the system 310 has a tissue graft 312, a cover 14, an anchor 316, and a suture 18. The cover 14 and the suture 18 may be substantially identical to those described previously, in connection with FIGS. 1 through 5 and 7 through 9. The tissue graft 312 differs from that of the previous figures in that, in addition to the central opening 42, it has a supplemental opening 344 through which the suture 18 is able to freely pass.

The anchor 316 of FIG. 10 has a suture attachment portion 346, a torque receiver 348, and a retention portion 350. The suture attachment portion 346 comprises a line lock designed to receive the suture 18 such that the suture 18 is movable through the suture attachment portion 346 along only one direction. The torque receiver 348 is designed to receive torque to facilitate insertion of the anchor 316 in a bone tunnel (not shown in FIG. 10). The retention portion 350 engages the walls of a bore of the bone tunnel to keep the anchor 316 in place.

As shown, the suture attachment portion 346 generally has the shape of a tab protruding from the remainder of the anchor 316. The suture attachment portion 346 has a first passageway 352, a second passageway 354, and a groove 356 that cooperate to retain the suture 18. The torque receiver 348 has a generally hexagonal cross sectional shape that may be received into a hexagonal cavity in the end of a tool (not shown) so that the tool can be used to transmit torque to the anchor 316. The retention portion 350 has a plurality of threads 358 that threadably engage the bore in response to torque from the tool and force tending to drive the anchor 316 into the bore.

The passageways 352, 354 cooperate to define a pathway 366 along which the first end 22 of the suture 18 can be inserted. As shown, the pathway 366 includes a compression portion 368 and a compressed portion 370. The pathway 366 extends from the first passageway 352 around the edge of the suture attachment portion 346 to define the compression portion 368, and then from the second passageway 354 between the compression portion 368 and the adjacent surface of the suture attachment portion 346 to define the compressed portion 270.

Once the suture 18 has been moved along the pathway 366, tension on the first end 22 of the suture 18 pulls the compression portion 368 away from the adjacent surface of the suture retention portion 346 to permit the compressed portion 370 to move, thereby allowing the suture 18 to continue moving along the pathway 366 toward the second end 22. However, tension on the second end 24 of the suture 18 pulls the compression portion 368 toward the adjacent surface of the suture retention portion 346 to press the compressed portion 370 securely against the suture retention portion 346, thereby keeping the suture 18 from moving along the pathway 366 toward the second end 24.

The groove 356 extends along the surface of the suture retention portion 346, from the first passageway 352 to the edge of the suture retention portion 346. Under tension exerted from the second end 24 of the suture 18, the compression portion 368 presses the compressed portion 370 into the groove 356. Pressure against the groove 356 causes the compressed portion 370 to receive additional bends, thereby strengthening the locking of the compressed portion 370.

Like the anchor 216, the anchor 316 provides one-way locking by permitting the suture 18 to move through the anchor 316 along one direction, but not in the opposite direction. Locking of the suture 18 by the anchor 316 is also automatic because the user need not actuate the anchor 216 to activate locking.

Figure 11:
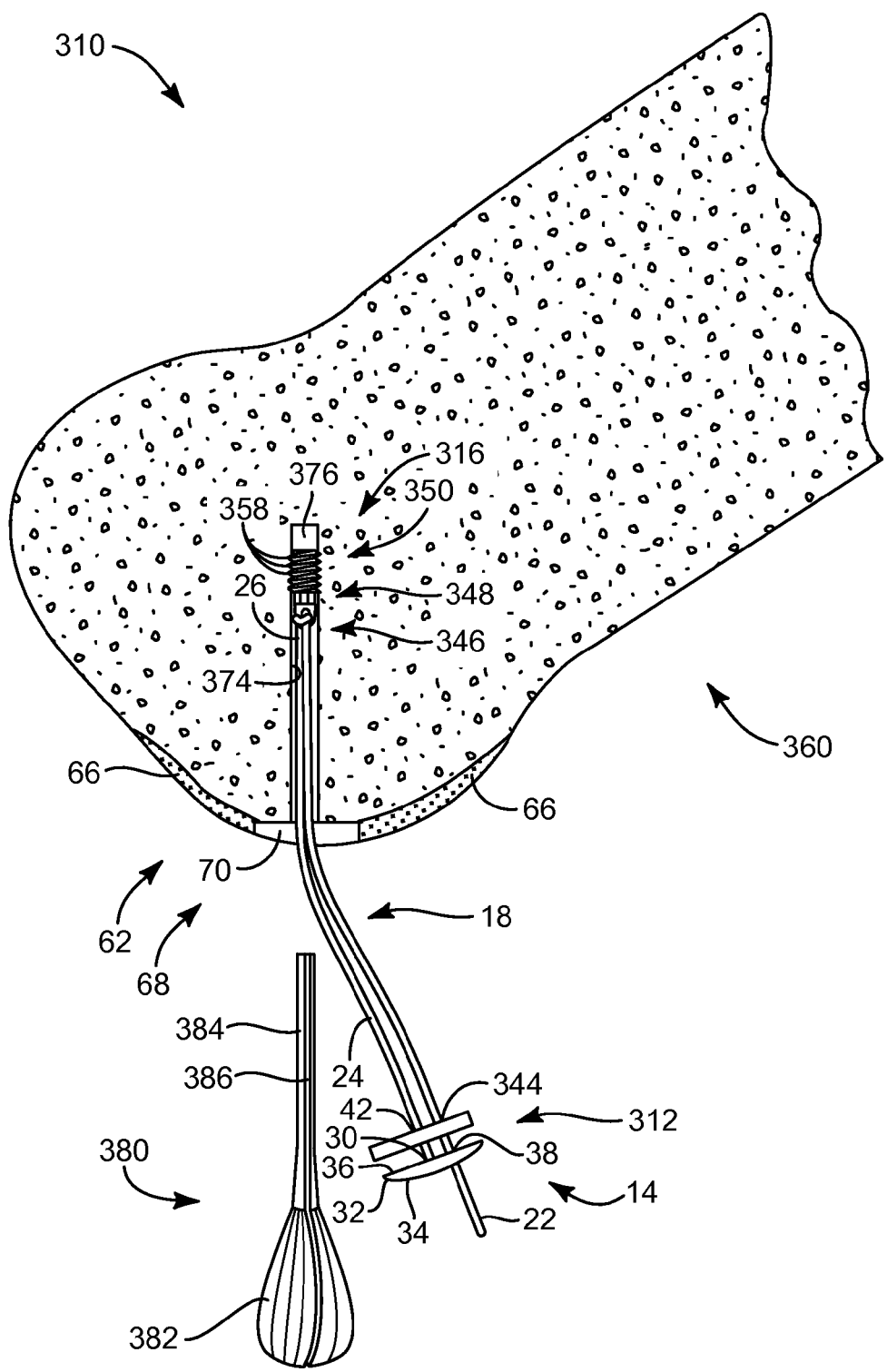
FIG. 11 is a side elevation, section view of a femur with a blind tunnel formed therein to receive the system of FIG. 10, in which the suture is fully drawn through the tunnel routed through the passageways through the anchor, and exits the tunnel again through the graft site.

Referring to FIG. 11, a side elevation, partially sectioned view illustrates a bone 372, in which the system 310 of FIG.

10 is partially installed. For clarity, the bone 372 has been sectioned, but the system 310 has not been sectioned. As shown, the bone 372 has a bore 374 that, unlike the bore 72 of the previous embodiments, only extends partway through the bone 372. Thus, the bore 374 has an end 376. The anchor 316 has been inserted into the bore 374 through the use of a tool 380. The tool 380 has a handle 382, a distal end 384, and a slit 386 extending along the length of the tool 380.

The handle 382 is shaped to be grasped by a user such as a surgeon. The distal end 384 has a narrow shape designed to permit the distal end 384 to fit within the bore 374. The distal end 384 also has a recess (not shown) with a hexagonal shape designed to receive the suture attachment portion 346 and the torque receiver 348. The retention portion 350 protrudes from the distal end 384.

In use, the first end 22 of the suture 18 may first be inserted through the central opening 42 of the tissue graft 312. Then, the first end 18 is inserted through the passageways 352, 354 of the suture attachment portion 346 of the anchor 316. The suture 18 moves relatively freely along the pathway 366 toward the first end 22, but cannot move through the passageways 352, 354 in the opposite direction. The first end 22 is inserted through the supplemental opening 344 of the tissue graft 312 and through one of the holes 38 of the cover 14.

Once the suture 18 has been routed as described above, the suture 18 is inserted into the tool 380 through the slit 386 such that the tissue graft 312 and the cover 14 are positioned proximally of the handle 382 and the anchor 316 is positioned distally of the distal end 384. Then, the anchor 316 is inserted into the distal end 384 such that the suture attachment portion 346 and the torque receiver 348 rest within the recess of the distal end 384. Then, the tool 380 is driven toward the bore 374 and rotated such that the anchor 316 threadably engages the bore 374. Once the anchor 316 has been inserted a sufficient distance into the bore, the suture 18 proximate the tissue graft 312 and the cover 14 is drawn out of the tool 380 through the slit 386. The tool 380 is then withdrawn from the bore 374 to provide the configuration illustrated in FIG. 11.

Figure 12:
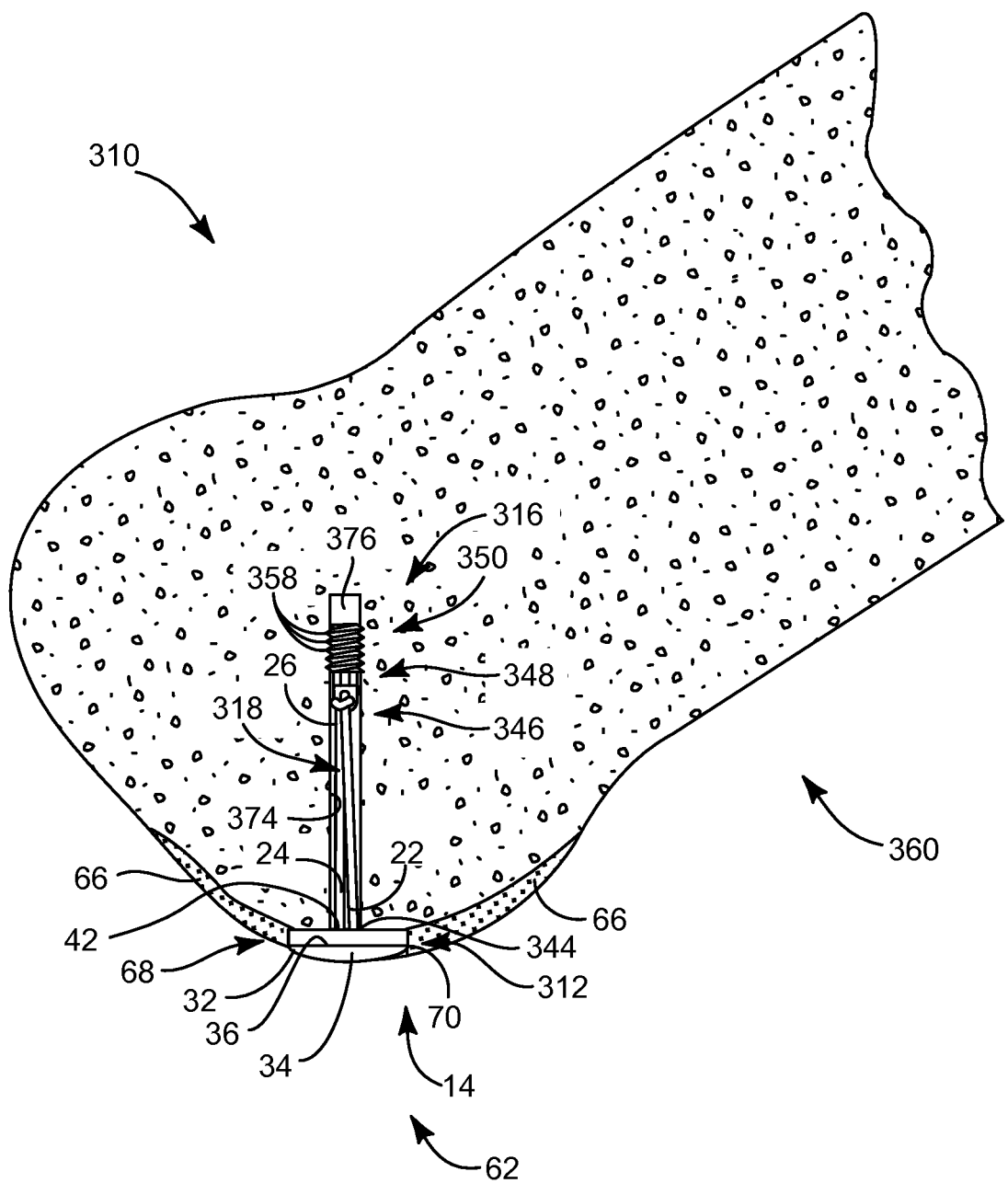
FIG. 12 is a side elevation, section view of the femur and the system of FIG. 10, in which the cover has been cinched against the graft site to retain the tissue graft by drawing the free end of the suture away from the anchor, with the suture locked with respect to the anchor to maintain tension in the suture.

Referring to FIG. 12, a side elevation, partially sectioned view illustrates the bone 372 with the system 310 of FIG. 10 fully installed in the bone 372 to retain the tissue graft 312. Again, the bone 372 has been sectioned, but the system 310 has not been sectioned. From the configuration of FIG. 11, the first end 22 may be drawn with respect to the anchor 316 to urge continued motion of the suture 18 along the pathway 366, toward the first end 22. Since the suture 18 passes redundantly through the graft site 68, this entails drawing the suture 18 through the graft site 68, rather than through an opposed end of the bore 374, as in previous embodiments. Advantageously, this avoids any invasive operations on the opposite side of the bone 372, thereby expediting recovery and reducing patient discomfort.

As in the previous embodiment, motion of the suture 18 toward the first end 22 may freely occur, while motion along the pathway 366 toward the second end 24 is prohibited. The anchor 316 remains stationary, but the suture 18 slides through the passageways 352, 354, through the supplemental opening 344, and through the corresponding hole 38 of the cover 14 until the suture 18 is taught within the bore 374. The tissue graft 312 is then sandwiched securely between the cover 14 and the graft site 68. The first end 22 of the suture 18 may be cut proximate the exposed end of the hole 38 of the cover 14 through which it passes to remove excess suture.

The present invention has particular relevance to surgery, and more particularly to articulation surface restoration. However, the principles, structures, and methods of the present invention may also be extended to other fields, including restoration of other types of tissue, or other types of articulation surfaces.

The present invention may be embodied in other specific forms without departing from its spirit or essential characteristics. For example, above are described various alternative examples of articulation surface restoration systems. It is appreciated that various features of the above-described examples can be mixed and matched to form a variety of other alternatives, each of which may have a different threading system according to the invention. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system comprising:
   a tether having a first portion and a second portion, wherein the second portion is configured to be coupled to a tissue graft, wherein the tether comprises a flexible member; and
   an anchor insertable into a tunnel formed in a bone proximate a graft site, wherein the anchor receives the first portion such that the first portion is slidable in a first direction with respect to the anchor, and the first portion is lockable by the anchor and by the first portion at any of a plurality of positions of the tether relative to the anchor to prevent sliding of the first portion in a second direction opposite to the first direction;
   wherein the anchor comprises a plurality of passageways that define a pathway along which the flexible member is slidable along in the first direction;
   wherein the tunnel passes through the bone between the graft site and an anchoring side on an opposite side of the bone from the graft site, wherein the anchor comprises a retention surface and an outer surface opposite the retention surface, wherein, when the anchor is inserted into the tunnel, the retention surface abuts the anchoring side, wherein the first portion slides in the first direction in response to tension tending to draw the flexible member from the outer surface.

2. The system of claim 1, wherein the flexible member is drawn from the anchoring side to slide the first portion in the first direction.

3. The system of claim 2, wherein the tunnel ends in an interior space of the bone, wherein the flexible member exits the anchor in a direction oriented toward the graft site, wherein the flexible member is drawn through the graft site, away from the anchor to slide the first portion in the first direction.

4. The system of claim 1, further comprising a cover attachable to the second portion, wherein the cover is formed substantially of a bioabsorbable material, wherein, when the cover is attached to the second portion and the second portion is coupled to the tissue graft, the cover abuts the tissue graft.

5. The system of claim 1, further comprising a cover attachable to the second portion wherein the cover has a fluid-permeable structure.

6. The system of claim 1, wherein the graft site is positioned within articular cartilage, wherein the tissue graft comprises a cartilage graft.

7. The system of claim 1, further comprising the tissue graft, wherein the tissue graft comprises a passageway through which the tether passes such that the tissue graft substantially encircles a length of the tether.

8. The system of claim 1, wherein the anchor automatically locks the first portion in response to tension on the tether tending to slide the first portion in the second direction.

9. A system for coupling an implant to an implant site proximate a bone, the system comprising:
   a tether having a first portion and a second portion, wherein the second portion is configured to be coupled to the implant, wherein the tether comprises a flexible member; and
   an anchor insertable into a tunnel formed in the bone, wherein the anchor receives the first portion such that the first portion slides in a first direction with respect to the anchor, and the first portion is automatically locked by the anchor and by the first portion at any of a plurality of positions of the tether relative to the anchor to prevent sliding of the first portion in a second direction opposite to the first direction;
   wherein the anchor comprises a plurality of passageways that define a pathway along which the flexible member is slidable along only the first direction;
   wherein the tunnel passes through the bone between the implant site and an anchoring side on an opposite side of the bone from the implant site, wherein the anchor comprises a retention surface and an outer surface opposite the retention surface, wherein, when the anchor is inserted into the tunnel, the retention surface abuts the anchoring side, wherein the first portion slides in the first direction in response to tension tending to draw the flexible member from the outer surface.

10. The system of claim 9, wherein the tunnel passes through the bone between the implant site and a tunnel end in an interior space of the bone, wherein the anchor comprises a retention portion and an attachment portion opposite the retention portion, wherein, when the anchor is inserted into the tunnel, the retention portion engages the tunnel end and the attachment portion faces the implant site, wherein the first portion slides in the first direction in response to tension tending to draw the flexible member from the implant site.

11. The system of claim 9, further comprising a cover attachable to the second portion, wherein the cover is formed substantially of a bioabsorbable material.

12. The system of claim 9, further comprising the implant, wherein the implant comprises a passageway through which the tether passes such that the implant substantially encircles a length of the tether.

* * * * *